United States Patent
Mitchell et al.

(10) Patent No.: US 10,192,998 B2
(45) Date of Patent: *Jan. 29, 2019

(54) ANALOG FLOATING-GATE ATMOMETER

(71) Applicant: Texas Instruments Incorporated, Dallas, TX (US)

(72) Inventors: Allan T. Mitchell, Heath, TX (US); Mark Eskew, Carrollton, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/848,741

(22) Filed: Dec. 20, 2017

(65) Prior Publication Data
US 2018/0130901 A1 May 10, 2018

Related U.S. Application Data

(62) Division of application No. 14/749,875, filed on Jun. 25, 2015, now Pat. No. 9,882,065.
(Continued)

(51) Int. Cl.
*H01L 29/78* (2006.01)
*A01G 25/16* (2006.01)
(Continued)

(52) U.S. Cl.
CPC .......... *H01L 29/788* (2013.01); *A01G 25/167* (2013.01); *G01N 15/0606* (2013.01);
(Continued)

(58) Field of Classification Search
CPC .......... G01N 15/0606; G01N 15/0656; G01N 2015/0026; G01N 2035/00881;
(Continued)

(56) References Cited

U.S. PATENT DOCUMENTS 3,540,277 A * 11/1970 Roth ...................... G01F 23/263
73/304 C
8,779,550 B2   7/2014 Liu et al.
(Continued)

OTHER PUBLICATIONS

Alam et al., Estimating Reference evatranspiration with an Atmometer, Mar. 2001, Researchgate, pp. 153-158.*
(Continued)

*Primary Examiner* — John Fitzgerald
*Assistant Examiner* — Truong D Phan
(74) *Attorney, Agent, or Firm* — Kenneth Liu; Charles A. Brill; Frank D. Cimino

(57) ABSTRACT

An atmometer system based on an analog floating-gate structure and circuit. The floating-gate circuit includes a floating-gate electrode that serves as a gate electrode for a transistor and a plate of a storage capacitor. A conductor element exposed at the surface of the integrated circuit is electrically connected to the floating-gate electrode; reference conductor elements biased to ground are also at the surface of the integrated circuit. In operation, the transistor is biased and moisture is dispensed at the surface. The drain current of the transistor changes as the floating-gate electrode discharges via the surface conductors and a conduction path presented by the moisture. The elapsed time until the drain current stabilizes indicates the evaporation rate.

17 Claims, 6 Drawing Sheets

Related U.S. Application Data

(60) Provisional application No. 62/018,248, filed on Jun. 27, 2014.

(51) Int. Cl.
*G01N 27/22* (2006.01)
*G01N 15/06* (2006.01)
*H01L 29/788* (2006.01)
*G01N 15/00* (2006.01)
*A01G 25/00* (2006.01)
*G01N 35/00* (2006.01)

(52) U.S. Cl.
CPC ....... *G01N 15/0656* (2013.01); *G01N 27/223* (2013.01); *A01G 25/00* (2013.01); *G01N 2015/0026* (2013.01); *G01N 2035/00881* (2013.01)

(58) Field of Classification Search
CPC ...... G01N 27/414; G01N 27/121; G01N 7/16; G01N 25/56; G01N 25/60; G01N 25/68; G01N 25/64; G01N 25/62; G01N 27/223; G01N 27/226; G01N 27/048; A01G 25/00; A01G 25/167; B82Y 10/00; B82Y 15/00; H01L 29/82; H01L 27/10852; H01L 27/10894; H01L 27/105; H01L 23/5223; H01L 27/0805; H01L 28/40; H01L 29/788; G01R 33/06; C10J 3/00; G01F 1/684

USPC ........ 73/29.01, 335.02, 25.05; 257/414, 252, 257/532, 296

See application file for complete search history.

(56) References Cited

U.S. PATENT DOCUMENTS

2006/0186901 A1* 8/2006 Itakura ................. G01N 27/223 324/689
2013/0221418 A1 8/2013 Mitchell et al.

OTHER PUBLICATIONS

Gu et al., "Kinetics of Evaporation and Gel Formation in Thin Films of Ceramic Precursors", Langmuir, vol. 30, No. 48 (American Chemical Society, 2014), pp. 14638-14647.

Gu et al., "Supporting Information for Kinetics of evaporation and gel formation in thin films of ceramic precursors", available at http://www.clemson.edu/ces/kornevlab/article/43si.pdf.

Ahuja et al., "A Very High Precision 500-nA CMOS Floating-Gate Analog Voltage Reference", J. Solid-State Circ., vol. 40, No. 12 (IEEE, Dec. 2005), pp. 2364-2372.

Alam et al., "Estimating Reference evapotranspiration with an Atmometer", Mar. 2001, Researchgate, pp. 153-158.

* cited by examiner

ANALOG FLOATING-GATE ATMOMETER

CROSS-REFERENCE TO RELATED APPLICATIONS

This application is a divisional of and claims priority to U.S. patent application Ser. No. 14/749,875, filed Jun. 25, 2015, which claims priority, under 35 U.S.C. § 119(e), of U.S. Provisional Application No. 62/018,248, filed Jun. 27, 2014, incorporated herein by this reference.

STATEMENT REGARDING FEDERALLY SPONSORED RESEARCH OR DEVELOPMENT

Not applicable.

BACKGROUND

This invention is in the field of electronic sensors. Embodiments disclosed in this specification include electronic sensors for sensing evaporation rate and relative humidity.

Atmometers are instruments for measuring the rate at which water evaporates from a wet surface into the atmosphere. Evaporation rate and related parameters are of particular importance in agriculture, among other industries. For example, knowledge of the rate at which plants transpire can assist the scheduling of irrigation activities, both in timing and in the amount of water applied to the crops. Efficient use of available water is, of course, especially important in arid regions, or those regions experiencing drought, where ground and surface water is at a premium.

Conventional atmometers operate by measuring the rate at which water is drawn from a reservoir to a surface exposed to the atmosphere. In one type of conventional atmometer, the exposed surface is a porous ceramic plate that is connected to the water reservoir by a tube. In the agricultural context, a canvas cover is typically provided over the ceramic plate to mimic the canopy of the crop of interest. As water evaporates from the ceramic plate, additional water is drawn through the tube from the reservoir to the plate. Measurement of the water level in the reservoir over time thus provides a measurement of the rate at which water is evaporating at the ceramic plate, from which the transpiration rate of the crop plant of interest can be inferred. The frequency at which measurements can be obtained from those conventional atmometers is necessarily limited, and as such these measurements are each essentially averaged over relatively long time periods (e.g., at least a few hours). In addition, because the evaporation rate measurement is typically obtained by visual inspection of the reservoir level, these conventional atmometers are not conducive to automation.

A recent trend, however, is the increasing deployment of networked communications among computer systems and other electronic devices themselves, absent human initiation or control of the communications. These machine-to-machine ("M2M") communications are now being carried out over a wide-area network, such a network now often referred to as the "Internet of Things" ("IoT"). In this context, the nature of the communications can differ significantly from conventional human-oriented Internet communications. The amount of data transmitted from one "machine" to another in a given transmission is often quite small (e.g., streaming video is not often involved), and is often not particularly time-sensitive. As such, the communications requirements for IoT can be somewhat relaxed. On the other hand, the number of M2M network nodes in the future is contemplated to be substantially larger than the number of nodes in the human-oriented Internet.

By way of further background, humidity is an important parameter in many industries, such as semiconductor processing, pharmaceutical and other chemical processing, petroleum refining, paper and textile production, agriculture, medicine, and food processing, to name a few. As such, conventional humidity sensors are used in equipment for these and other industries, examples of such equipment including respiratory equipment, sterilizers, incubators, ovens, dryers and dessicators, condensation prevention equipment, and monitoring equipment such as soil moisture monitors and building environmental control.

By way of further background, Gu et al., "Kinetics of Evaporation and Gel Formation in Thin Films of Ceramic Precursors", *Langmuir*, Vol. 30, No. 48 (American Chemical Society, 2014), pp. 14638-47 (see "Supporting Information for Kinetics of evaporation and gel formation in thin films of ceramic precursors", available at http://www.clemson.edu/ces/kornevlab/article/43si.pdf), describes the evaporation mechanism as a diffusion mechanism that depends on the water vapor concentration gradient between the surface of the evaporating water droplet (i.e., at 100% relative humidity) and the ambient atmosphere (i.e., at the ambient relative humidity). This mechanism is expressible as a temperature-dependent diffusion equation, from which the ambient relative humidity can be determined from measurements of the evaporation rate and the temperature.

BRIEF SUMMARY

Disclosed embodiments provide a device, system, and method for rapidly and frequently measuring evaporation rate.

Disclosed embodiments provide such a device, system, and method that can be implemented as an automated sensor and deployed in a machine-to-machine (M2M) networked system.

Disclosed embodiments provide such a device, system, and method suitable for rapidly and frequently measuring relative humidity.

Disclosed embodiments provide such a device that can be fabricated using conventional integrated circuit manufacturing technology, and thus at low cost.

Disclosed embodiments provide such a device, system, and method that can be calibrated and thus provide repeatable and reliable measurements.

Other objects and advantages of the disclosed embodiments will be apparent to those of ordinary skill in the art having reference to the following specification together with its drawings.

According to certain embodiments, an integrated circuit including an analog floating-gate structure is arranged in a system for sensing evaporation rate. A floating-gate electrode serves as a gate of a metal-oxide-semiconductor (MOS) transistor and is connected to a conductor element, for example in the form of a metal pad, that is disposed at the surface of the integrated circuit. One or more reference conductor elements are also disposed at the surface, separated from the conductor element coupled to the floating-gate electrode, and biased to a reference voltage such as ground. With the drain and gate of the transistor biased so that drain current is conducted, moisture is dispensed at the surface of the integrated circuit. The drain current is monitored over time, as charge on the floating-gate electrode is discharged to the reference conductor electrodes via the dispensed moisture. The evaporation rate of the moisture can be inferred from the time elapsed from dispensing of the moisture until the drain current reaches a steady-state equilibrium.

According to an embodiment, the analog floating-gate structure is implemented into a system that also includes control logic for controlling the bias and operation of the analog floating-gate structure to obtain the evaporation rate measurement, along with a mechanism for dispensing moisture at the integrated circuit surface.

According to an embodiment, the system also includes processor circuitry that calculates relative humidity of the ambient atmosphere by combining the measured evaporation rate and a temperature measurement.

BRIEF DESCRIPTION OF THE SEVERAL VIEWS OF THE DRAWING

FIG. 3b is a timing diagram illustrating the operation of the analog floating-gate equivalent circuit of FIG. 3a.

DETAILED DESCRIPTION

The one or more embodiments described in this specification are implemented into an atmometer system or device implemented in a networked arrangement, such as according to the "Internet of Things" (IoT), as it is contemplated that such implementation is particularly advantageous in that context. However, it is also contemplated that concepts of this invention may be beneficially applied to in other applications, such as stand-alone devices or as integrated into manufacturing, environmental, or other equipment for which measurement of evaporation rate is useful. Accordingly, it is to be understood that the following description is provided by way of example only, and is not intended to limit the true scope of this invention as claimed.

As mentioned above in the Background of the Invention, it is contemplated that distributed networked systems consisting of a number of sensors and controllers that each contain significant computational capacity and are capable of M2M communication with one another will be widely deployed over the coming years. In these networks, the number of nodes (i.e., the sensors, controllers, or both) in such a network can range from several nodes to thousands of nodes, depending on the particular application. These networks have become attractive in the contexts of facilities management (e.g., for environmental control and security management) and industrial control (e.g., control of motors and valves). In particular, it is contemplated that the embodiments described in this specification may be particularly useful in agricultural, environmental, and manufacturing contexts.

Figure 1A:
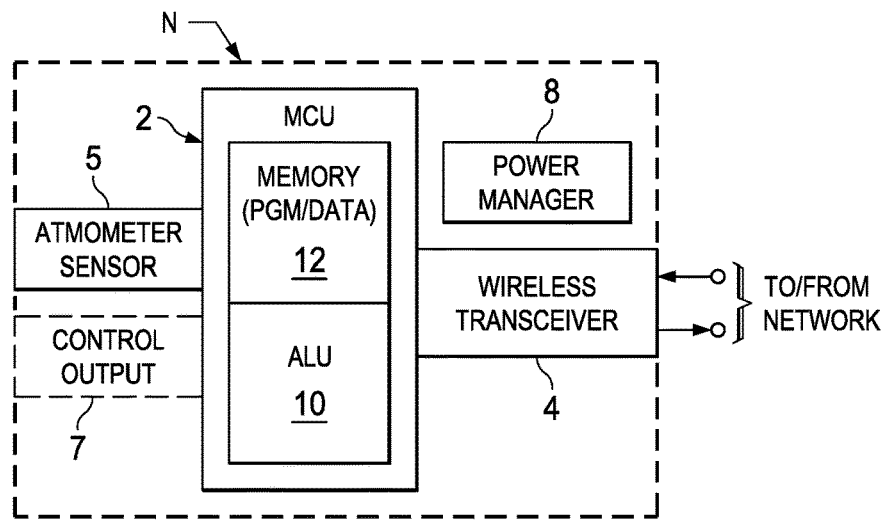
FIG. 1a is an electrical diagram, in block form, of a sensor and controller node as may be deployed in a distributed network system, according to some embodiments.

FIG. 1a illustrates, by way of example, the high-level architecture of a sensor node N into which embodiments of this invention may be implemented, by way of example. Node N is intended for deployment into a distributed networked system, along with nodes in that system constructed by similar or alternative architectures, perhaps depending on the function. It is contemplated that those skilled in the art having reference to this specification will be readily able to implement the appropriate hardware and software for realizing embodiments of this invention as suitable for particular applications, without undue experimentation.

Node N in this embodiment of the invention corresponds to a programmable subsystem including embedded microcontroller unit (MCU) 2 in combination with various peripheral functions. For example, node N may be physically realized by way of a single circuit board on which MCU 2 will be mounted, along with other integrated circuits and discrete components as desired, housed in an appropriate housing or enclosure suitable for its environment. Alternatively, node N may be realized by way of multiple circuit boards, as a single integrated circuit, or as a part of a larger electronic system, depending on its functionality. In the architecture of node N of FIG. 1a, communication with other nodes and perhaps with a host computer system are carried out by way of wireless transceiver 4, constructed and operating in the appropriate manner for the particular communications facility being used. If communication is to be carried out wirelessly, any one of a number of conventional protocols and physical layer standards, including IEEE 802.11a/b/g/n etc., Bluetooth, and Bluetooth 4.0 (i.e., Bluetooth Low Energy, or "BLE"), may serve as that communications facility; alternatively, transceiver 4 may be configured for communication over Ethernet or another type of wired network.

According to this embodiment, node N also includes one or more input/output functions for interacting with the physical environment external to that node. One such function is atmometer sensor 5, which is coupled to and controlled by MCU 2. Optionally, control output circuit 7 may also be provided in node N, coupled to and controlled by MCU 2 to realize a controller function. Examples of control output circuit 7 include analog output driver circuitry, serial and parallel digital outputs, pulse-width-modulated (PWM) output driver circuitry, driver circuitry for an alarm or an annunciator, and LED drivers, to name a few. The particular numbers and functions of input/output functions (e.g., atmometer sensor function 5 and control output circuit 7) depend on the conditions and operations that node N is to carry out in the networked system. Such additional sensor and controller functions may be additional instances of the same function, or may be configured as other functions. Other sensor functions that may additionally be realized at node N include temperature sensors, motion sensors, humidity sensors, transducers of various types as suitable in industrial instrumentation, cameras, thermal imaging sensors, photosensors, and the like.

In the example of FIG. 1a, node N also includes power manager function 8, which controls the powering of the various functions within the node. For example, node N may be powered by any one or more sources including wired power (e.g., power over USB, DC output from a rectifier or micro-grid), battery power, solar power, wireless power transfer (e.g., over the wireless communications facility or separately), and the like.

In this embodiment, MCU 2 in node N is configured to include certain functions particular to the construction and operation of this embodiment of the invention, for example by way of logic circuitry programmed to execute program instructions stored in memory resource 12 or received over the communications facility via wireless transceiver 4. For example, at least a portion of this programmable logic is represented by ALU 10, which operates in combination with memory resource 12 that is also implemented within MCU 2 in this example. In some embodiments, MCU 2 is realized by any one of a number of microcontroller or microprocessor devices available in the industry, examples of which include those of the C2xxxx and CORTEX microcontroller families available from Texas Instruments Incorporated. Other microcontrollers and microprocessors of similar computational capacity, or custom logic circuitry, may alternatively be used for MCU 2, so long as adequate computational capacity is provided. It is contemplated that those skilled in the art having reference to this specification will be readily able to select and implement the appropriate device or circuitry for use as MCU 2 for the particular application.

In this architecture, memory resource 12 stores both program instructions executable by ALU 10, and also data upon which ALU 10 carries out those program instructions. Memory resource 12 can be realized by one or more memories within MCU 2 or external to MCU 2, and by a variety of memory technologies, including either or both of volatile memory (e.g., static random-access memory) and non-volatile memory (e.g., flash memory). Program and data memory may occupy separate memory address spaces, or may be contained within a single memory space. For the example of MCU 2 implemented as a C2xxx microcontroller, a modified Harvard architecture is employed by way of which program and data occupy separated regions of a global memory address space, but can be accessed by way of separate hardware pathways.

Node N and MCU 2 are also contemplated to include other circuitry and functions beyond those shown in FIG. 1a, such other circuitry and functions suitable to its functionality as a stand-alone microcontroller. Examples of such other circuitry and functions input and output drivers, analog-to-digital converters, digital-to-analog converters, clock circuits, voltage regulators, among others. These circuits may be also be involved in the operation and execution of program instructions by MCU 2 and the other functions of node N. It is contemplated that those skilled in the art having reference to this specification will readily comprehend other necessary support circuitry included within MCU 2.

Figure 1B:
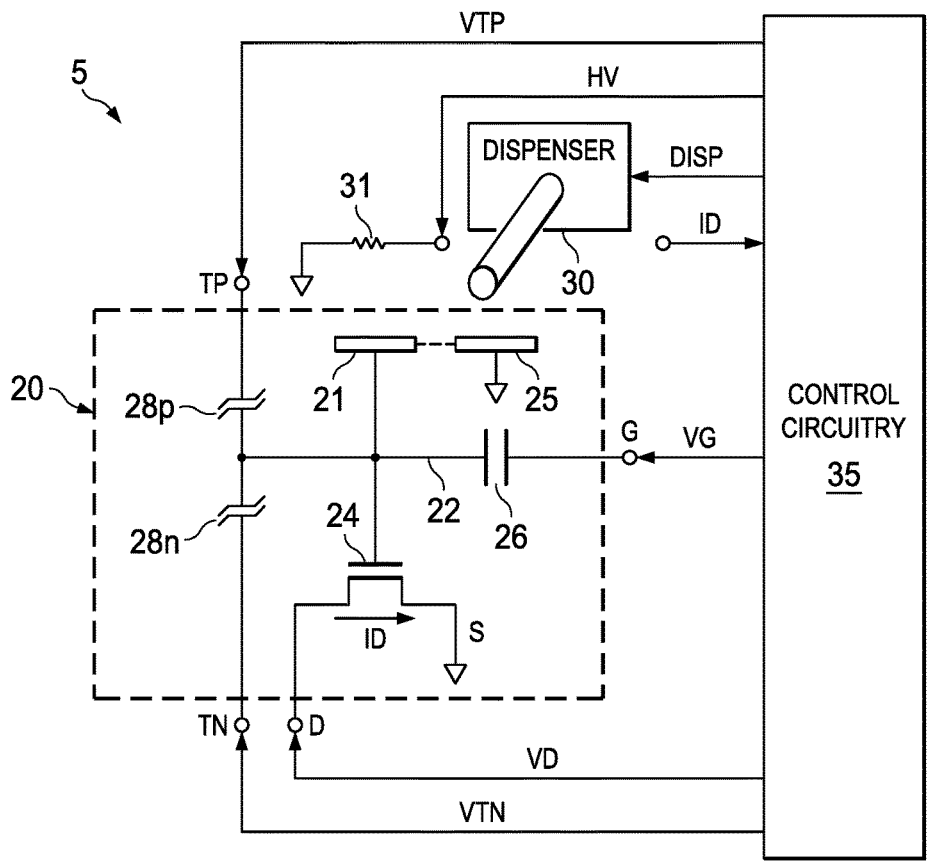
FIG. 1b is an electrical diagram, in block form, of an atmometer sensor in the node of FIG. 1a according to embodiments.

Referring now to FIG. 1b, the architecture of atmometer sensor 5 according to an embodiment will now be described. In this example, atmometer sensor 5 is arranged in the form of a subsystem, including integrated circuit 20 in which a floating-gate circuit is implemented, in combination with other functions such as moisture dispenser 30, optional heater 31, and control circuitry 35. As evident from FIG. 1b, control circuitry 35 is coupled to various nodes of integrated circuit 20, to moisture dispenser 30, and to heater 31, and will apply control signals and monitor electrical parameters to carry out the functions described in further detail below, those functions including the dispensing of moisture onto the surface of integrated circuit 20 by moisture dispenser 30, the bias and monitoring of components of integrated circuit 20, and the optional heating of the surface of integrated circuit 20 by heater 31. Control circuitry 35 may be realized in whole or in part as separate circuitry deployed within the subsystem of atmometer sensor 5 and in communication with MCU 2, or within MCU 2 itself. In some realizations, all or part of control circuitry 35 may be implemented into integrated circuit 20 itself, along with the analog floating-gate device. In any case, it is contemplated that those skilled in the art having reference to this specification will be readily able to implement control circuitry 35 in the manner appropriate for carrying out the functions described herein, using the available and appropriate technology for the particular architecture to be used.

Integrated circuit 20 includes an analog floating-gate circuit and structure in connection with which embodiments of this invention may be used. This analog floating-gate circuit includes an electrically floating electrode, namely floating-gate electrode 22 in the arrangement of FIG. 1b, that serves multiple functions. One function of analog floating-gate electrode 22 in this circuit of FIG. 1b is as a plate of storage capacitor 26. According to this embodiment, another plate of storage capacitor 26 receives a gate voltage VG from control circuitry 35 at terminal G, such that charge can be externally applied to and stored by storage capacitor 26. Another function of floating-gate electrode 22 is as the gate of metal-oxide-semiconductor (MOS) transistor 24. In the example of FIG. 1b, the drain of transistor 24 at drain terminal D receives drain voltage VD from control circuitry 35, and the source of transistor 24 at source terminal S is biased to a reference voltage, namely ground in this example. In this arrangement, gate voltage VG applied at terminal G by control circuitry 35 will capacitively couple to floating-gate electrode 22 via storage capacitor 26, with that voltage establishing the voltage at the gate of MOS transistor 24, and thus the extent to which transistor 24 conducts between its drain D and its source S for a given drain-to-source voltage VD.

In this arrangement, floating-gate electrode 22 also serves as a plate of each of tunnel capacitors 28p, 28n. Tunnel capacitors can apply charge to or remove charge from floating-gate electrode 22, "programming" it to a particular analog state. In the example of integrated circuit 20, the plate of tunnel capacitor 28p opposite that of electrode 22 is connected to a terminal TP, while an opposing plate of tunnel capacitor 28n is connected to a terminal TN. The capacitor dielectric for tunnel capacitors 28p, 28n is contemplated to be relatively thin, to allow mechanisms such as Fowler-Nordheim tunneling to transfer charge between terminals TP, TN and floating-gate electrode 22, depending on the bias. While, as noted above, tunnel capacitors 28p, 28n permit both the programming of stored charge onto floating-gate electrode 22 and the removal of that charge ("erase"), it is contemplated that only one of these tunnel capacitors 28p, 28n may be implemented in some implementations.

In its general operation as an analog floating-gate device, the "programming" of floating-gate electrode 22 is carried out by application of a pulse of an appropriate negative voltage to terminal TN relative to the voltage at terminal TP and to the ground reference voltage at the opposite plate of storage capacitor 26, to cause electrons to tunnel through tunnel capacitor 28n. Because of the voltage divider formed by capacitors 28n, 28p, 26, most of that programming voltage will appear across tunnel capacitor 28n, enabling electrons to tunnel through its capacitor dielectric to analog floating-gate electrode 22, and become trapped at floating-gate electrode 22. Conversely, electrons can be removed ("erased") from floating-gate electrode 22 by applying an appropriate positive voltage at terminal TP relative to terminal TN and to the ground reference voltage at the opposite plate of storage capacitor 26. Again, the voltage divider of capacitors 28n, 28p, 26 will result in most of that voltage appearing across tunnel capacitor 28p, causing electrons that are trapped on floating-gate electrode 22 to tunnel through its capacitor dielectric to terminal TP. In the analog sense, the duration of the program and erase pulses can be adjusted to precisely set the charge state at floating-gate electrode 22. Following programming and erasure, as the case may be, the extent to which charge is trapped on floating-gate electrode 22 will establish a voltage across storage capacitor 26, and thus a gate voltage for MOS transistor 24 that controls its conduction.

As evident from the above description and from FIG. 1b, control circuitry 35 is coupled to the various terminals of the floating-gate device of integrated circuit 20, including to terminals G, D, TP, TN so as to apply corresponding voltages VG, VD, VTP, VTN, respectively. In this example, control circuitry 35 monitors the drain current ID conducted by transistor 24, for example by detecting the current drawn by its bias of drain voltage VD to directly measure drain current ID. Alternatively, transistor 24 may drive an analog circuit or other function, such as an amplifier, from which control circuitry 35 obtains a measurement of drain current ID of transistor 24. Also according to this embodiment, control circuitry 35 also includes a timer function, such as a clocked counter or other conventional timer, to provide a time base for the monitoring of drain current ID over time, as described below.

In this embodiment as shown in FIG. 1b, integrated circuit 20 also includes conductor element 21 that is electrically connected to floating-gate electrode 22, and reference conductor element 25 that is coupled to a reference voltage, such as ground, but is otherwise electrically isolated from conductor element 21 and the other nodes of the analog floating-gate device in integrated circuit 20. As will be evident from the following description, these conductor elements 21, 25 are constituted by metal pads at the surface of integrated circuit 20 that are exposed to the ambient environment of the device.

Figure 2A:
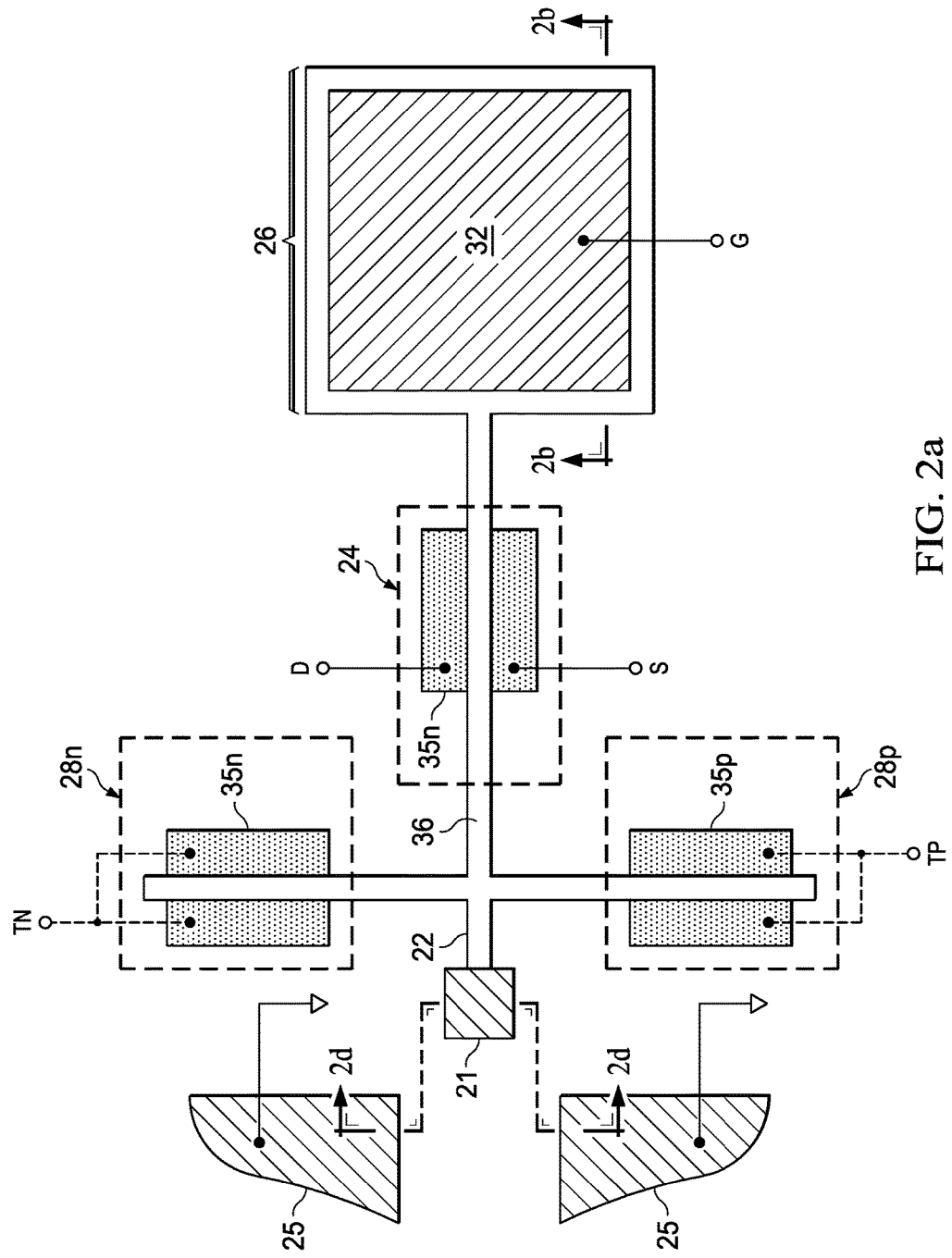
FIGS. 2a and 2c are plan views.
Figure 2B:
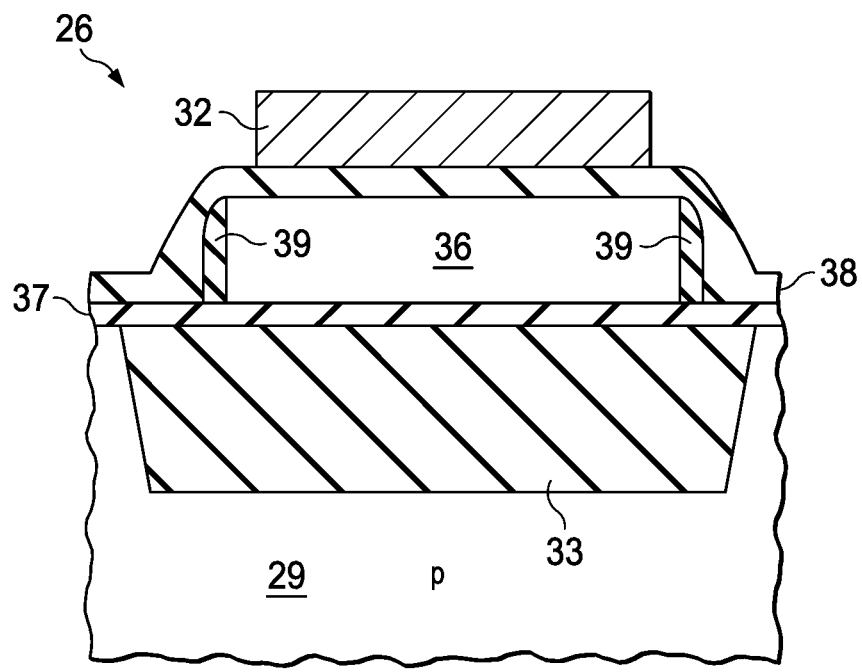
FIGS. 2b and 2d are cross-sectional views, of an analog floating-gate integrated circuit implemented in the atmometer sensor of FIG. 1b according to embodiments.

FIG. 2a illustrates, in plan view, an example of the construction of an analog floating-gate structure such as may be used to implement the circuit of FIG. 1b, and in connection with which embodiments may be used. FIGS. 2b and 2d illustrate certain elements in that structure in cross-section. It is contemplated that this floating-gate structure may be fabricated by way of conventional manufacturing technology, including at those process nodes extending into the sub-micron regime. It is therefore contemplated that those skilled in the art having reference to this specification will be readily able to adapt the structure of FIGS. 2a through 2d in the desired manufacturing technology, without undue experimentation.

As shown in FIG. 2a, floating-gate electrode 22 is constructed of polycrystalline silicon (polysilicon) element 36, which extends over the surface of a semiconductor wafer (or over a semiconductor surface layer, in the silicon-on-insulator context) in forming multiple devices or components. Polysilicon element 36 is typically doped to a desired conductivity type and concentration, to be conductive to the desired extent; for example by way of n-type doping for this example in which MOS transistor 24 is n-channel. Polysilicon element 36 has a widened portion at its end serving as a lower plate of storage capacitor 26, and is otherwise narrower, for example at a minimum feature size for the manufacturing technology. The cross-section of storage capacitor 26 shown in FIG. 2b shows the lower plate portion of polysilicon element 36 as overlying trench isolation dielectric structure 33. Gate dielectric 37, for example formed of deposited or thermal silicon dioxide, is disposed between the surface of isolation dielectric structure 33 and polysilicon element 36, and will also underlie polysilicon element 36 at those locations at which it overlies active regions (i.e., at transistor 24 and tunnel capacitors 28p, 28n). In this example, the surface into which isolation dielectric structure 33 is formed is the top surface of p-type silicon substrate 29. Upper plate 32 of storage capacitor 26 is formed of a metal such as tantalum nitride, and overlies the widened portion of polysilicon element 36 at this location. In this embodiment of the invention, capacitor dielectric 38 is formed of one or more dielectric layers, for example silicon nitride, silicon dioxide, or a combination of these or other dielectric materials.

As shown in FIG. 2a, transistor 24 and tunnel capacitors 28p, 28n are constructed along those portions of polysilicon element 36 that overlie active regions (i.e., that do not overlie isolation dielectric structures 33). Specifically, MOS transistor 24 is defined at that portion of polysilicon element 36 overlying an active region of p-type substrate 29, with gate dielectric 37 disposed between polysilicon element 36 and that active region. The source and drain of transistor 24 are formed by heavily-doped n-type source/drain regions $35_n$ implanted and diffused into the p-type active region on opposite sides of polysilicon element 36 in the conventional self-aligned fashion. Top side contacts from an overlying metal conductor, and corresponding to terminals D, S as in the circuit of FIG. 1b, are made through an interlevel dielectric layer to source/drain regions $35_n$.

Tunnel capacitors 28n, 28p are constructed in the conventional manner for floating-gate devices. In this embodiment, tunnel capacitor 28n is constructed essentially similarly as n-channel MOS transistor 24, but where polysilicon element 36 overlies an instance of an isolated p-type well, for example a p-well isolated from the underlying substrate by a buried n-type layer and an n-well ring. Gate dielectric 37 is formed between polysilicon element 36 and the surface of the p-well to serve as the capacitor dielectric, and heavily-doped n-type source/drain regions $35_n$ are formed into the isolated p-well in a self-aligned manner. Terminal TN is connected via a top-side contact to the isolated p-well in which these source/drain regions $35_n$ are formed, so tunnel capacitor 28n operates as a capacitor rather than a transistor, but with source/drain regions $35_n$ serving as sources of electrons when a negative bias is applied to terminal TN. Tunnel capacitor 28p is constructed essentially similarly as tunnel capacitor 28n, but at a location at which polysilicon element 36 overlies gate dielectric 37 at the surface of an n-well formed into substrate 29. Terminal TP is connected to this n-well by a top-side contact, and p-type source/drain regions $35_p$ that are formed on either side of polysilicon element 36 act as a sources of holes when a positive bias is applied to terminal TP. Tunnel capacitors 28p, 28n may of course be constructed according to other arrangements as suitable for particular implementations and manufacturing technologies.

In the example shown in FIG. 2a, the difference in relative area between tunneling capacitors 28p, 28n, on one hand, and storage capacitor 26, on the other hand, along with any differences in the capacitor dielectric materials and thicknesses, will be reflected in the relative capacitances between these elements. Because the capacitance of storage capacitor 26 is substantially larger than the capacitances of tunnel capacitors 28n, 28p (and also the parasitic gate-to-active capacitance of transistor 24), tunneling of electrons can be achieved at reasonable bias voltages to avoid damage or breakdown. This disparity in capacitive coupling is contemplated to provide excellent programming and erase performance.

Many variations in the electrical and physical construction of an analog floating-gate circuit in an integrated circuit, relative to that described above, are contemplated. From an electrical standpoint, such variations include circuits such as a reference circuit arranged as a dual floating-gate differential amplifier circuit, as known in the art. As mentioned above, examples of other analog floating-gate circuits include analog memory devices, and digital electrically programmable memory cells (including cells that may be set into one of more than two possible states, reflecting a multiple-bit data value). From a construction standpoint, such variations include other arrangements of the floating-gate device, including polysilicon-to-polysilicon floating-gate capacitors, polysilicon-to-active capacitors, and the like, and including floating-gate devices that are programmable by other mechanisms besides Fowler-Nordheim tunneling. Examples of such alternative structures are described in U.S. Patent Application Publication No. US 2013/0221418 and U.S. Pat. No. 8,779,550, both commonly assigned herewith, and in Ahuja et al., "A Very High Precision 500-nA CMOS Floating-Gate Analog Voltage Reference", *J. Solid-State Circ.*, Vol. 40, No. 12 (IEEE, December 2005), pp. 2364-72, all such references incorporated herein by reference. It is contemplated that those skilled in the art having reference to this specification will be readily able to realize these, and other, variations as appropriate for particular circuit applications, without undue experimentation.

Figure 2C:
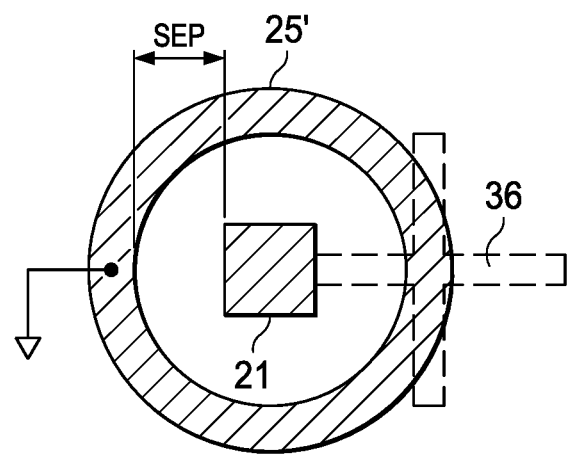
Figure 2D:
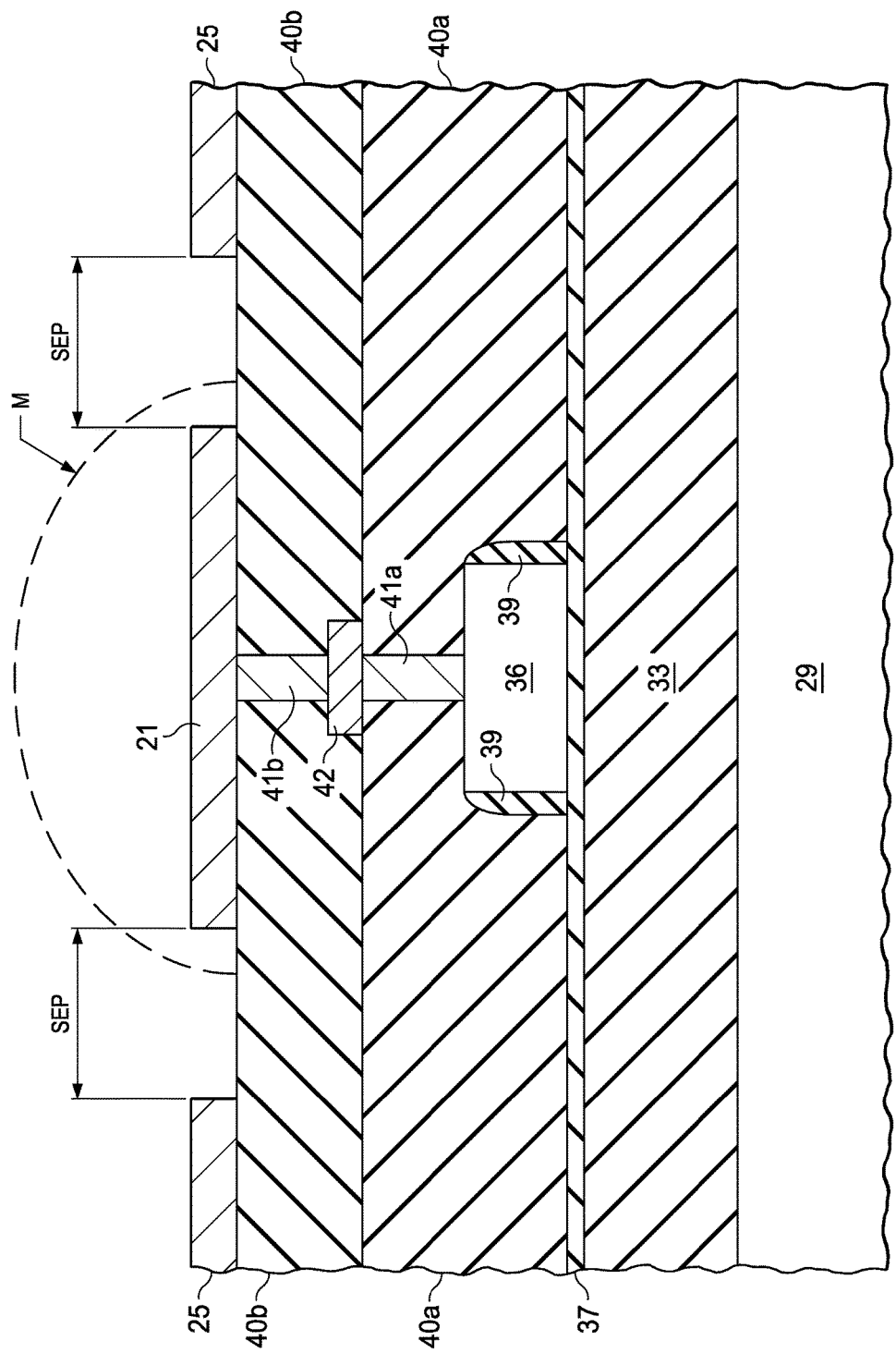

Also as shown in FIGS. 2a, 2c, and 2d and as described above, conductor element 21 is formed as a metal pad at the surface of integrated circuit 20 to be in electrical contact with polysilicon element 36 (i.e., floating-gate electrode 22). In this example, first interlevel insulator 40a overlies polysilicon element 36, with conductive plug 41a disposed in a via in that insulator 40a and in contact with polysilicon element 36 as shown. Conductive pad 42, formed of a metal (i.e., in the first metal level) or another conductor material, is disposed at the surface of first interlevel insulator 40a and in contact with plug 41a. Similarly, second interlevel insulator layer 40b overlies first interlevel insulator 40a, with conductive plug 41b formed in a via through layer 40b to contact conductive pad 42. Conductor element 21 in this example is formed at the surface of second interlevel insulator 40b, at a location overlying and in contact with conductive plug 41b. As such, conductor element 21 is in electrical contact with polysilicon element 36, i.e. floating-gate electrode 22, by the series connections of plugs 41a, 41b and pad 42. While plugs 41a, 41b and pad 42 are all illustrated as directly overlying one another in the example of FIG. 2d, it is of course contemplated that plugs 41a, 41b may be laterally separated from one another (i.e., contacting conductive pad 42 at different locations along its length) if desired. In addition, while the example of FIG. 2d shows two metal levels (pad 42 and element 21) being used for this structure, it is of course contemplated that additional metal levels may be included in the various layers between conductive element 21 and polysilicon element 36, as known in the art. In any event, according to these embodiments, conductive element 21 is exposed at the surface of the integrated circuit, either above the top insulator layer (layer 40b in the example of FIG. 2d), or alternatively exposed through an opening in a protective overcoat or other overlying insulator layer.

One or more reference conductive elements 25 are also provided at the surface of the integrated circuit. These reference conductive elements 25 are contemplated to be one or more metal features formed in the same conductive layer as conductive element 21, and near to but spaced apart from conductive element 21. In the example shown in FIG. 2a, reference conductive elements 25 are in the form of metal pads that are significantly larger in area than conductive element 21; in this arrangement, it is contemplated that these multiple metal pads will typically surround conductive element 21. According to another embodiment as shown in FIG. 2c, a single reference conductive element 25' is in the form of a metal ring that encircles conductive element 21. In any case, reference conductive elements 25, 25' (collectively referred to as reference conductive elements 25) are each separated from conductive element 21 by some distance SEP, and as such are not in direct electrical contact with conductive element 21 (nor in contact with any other node of the analog floating-gate circuit, for that matter). It is contemplated that one or more reference conductive elements 25 that surround conductive element 21 on all sides will provide repeatable and consistent results. Each reference conductive element 25 is in contact with a conductor or a semiconductor region that will, in operation, be at a reference voltage such as ground. As in the case of conductive element 21, each reference conductive element 25 will be exposed at the surface of the integrated circuit, either above the top insulator layer (layer 40b in the example of FIG. 2d), or alternatively exposed through an opening in a protective overcoat or other overlying insulator layer. If the latter, it is believed to be preferable that the entire region of the surface of the integrated circuit containing conductive element 21 and nearby reference conductive elements 25 be exposed within a single opening in the protective overcoat.

According to these embodiments, as will be described in further detail below, the operation of atmometer sensor 5 is based on the electrical effects of the evaporation of moisture dispensed at the surface of integrated circuit 20 by moisture dispenser 30, in response to a signal from control circuitry 35. This moisture at the surface of integrated circuit 20 both in liquid form (e.g., moisture droplet M in FIG. 2d) as dispensed, and also in the form of the moist air produced by the evaporation of that moisture, provides a conduction path between conductor element 21 and reference conductor elements 25. Charge from floating-gate electrode 22 will conduct via this conduction path to the reference voltage at reference conductive elements 25 until the moisture has evaporated to the extent that the conduction path disappears. The discharge of floating-gate electrode 22 caused by this conduction will be reflected in changes in the drain current ID conducted by transistor 24 under bias, from which the evaporation rate can be inferred. More specifically, because charge will no longer be conducted from floating-gate electrode 22 once moisture has evaporated from the surface, the time at which the drain current ID stabilizes following the dispensing of the moisture will indicate the evaporation rate at the location of atmometer sensor 5, under the current environmental conditions.

Referring back to FIG. 1b, in order for atmometer sensor 5 to provide repeatable measurements of evaporation rate, moisture dispenser 30 should be capable of repeatably dispensing moisture droplets, repeatable in the sense that the droplet does not vary appreciably in size or center location from measurement to measurement. One type of apparatus suitable for use as moisture dispenser 30 in these embodiments is an ink-jet printer head type of dispenser, as this type of dispenser is capable of dispensing liquid droplets of consistent size to precise locations; it is also contemplated that other conventional types of dispensing apparatuses, such as controllable atomizers and the like, may alternatively be used. Good repeatability also requires that the dispensed moisture be of consistent conductivity, and preferably relatively low conductivity to facilitate accuracy in the evaporation rate measurement. It is contemplated that distilled water will be suitable for use as the medium dispensed by moisture dispenser 30 in these embodiments; additional precision can be obtained by measuring the conductivity of the distilled water or other medium prior to loading moisture dispenser 30.

As mentioned above, optional heater 31 may be implemented in atmometer sensor 5 to dry the surface of integrated circuit 20 between measurements. It is contemplated that various types of elements may be used as heater 31, including one or more polysilicon or diffused resistors in integrated circuit 20 itself, or a heating element external to integrated circuit 20 within atmometer sensor 5 and under the control of control circuitry 35. If implemented, however, heater 31 should be controlled by control circuitry 35 to not alter the environmental conditions at the surface of integrated circuit 20 at the time that measurements are made; as such, it is contemplated that heater 31 will be only temporarily activated between measurements, perhaps with time allotted for atmometer sensor 5 to return to an equilibrium condition relative to the surrounding environment.

Figure 3A:
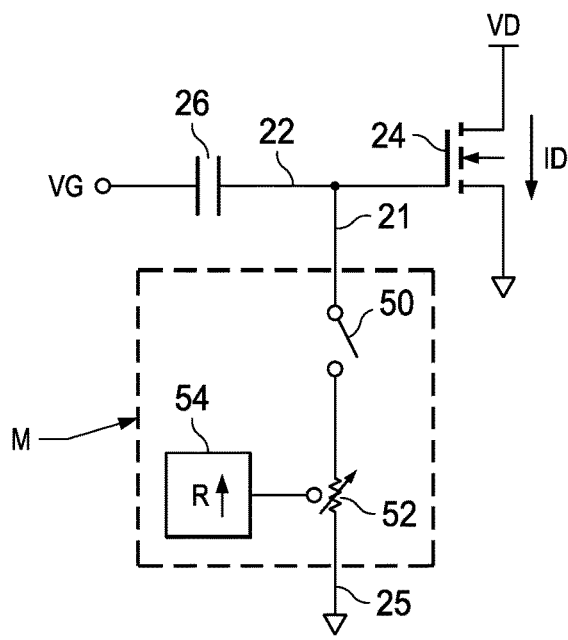
FIG. 3a is an electrical diagram, in schematic form, of an equivalent circuit for the analog floating-gate structure of FIGS. 2a through 2d according to embodiments.
Figure 3B:
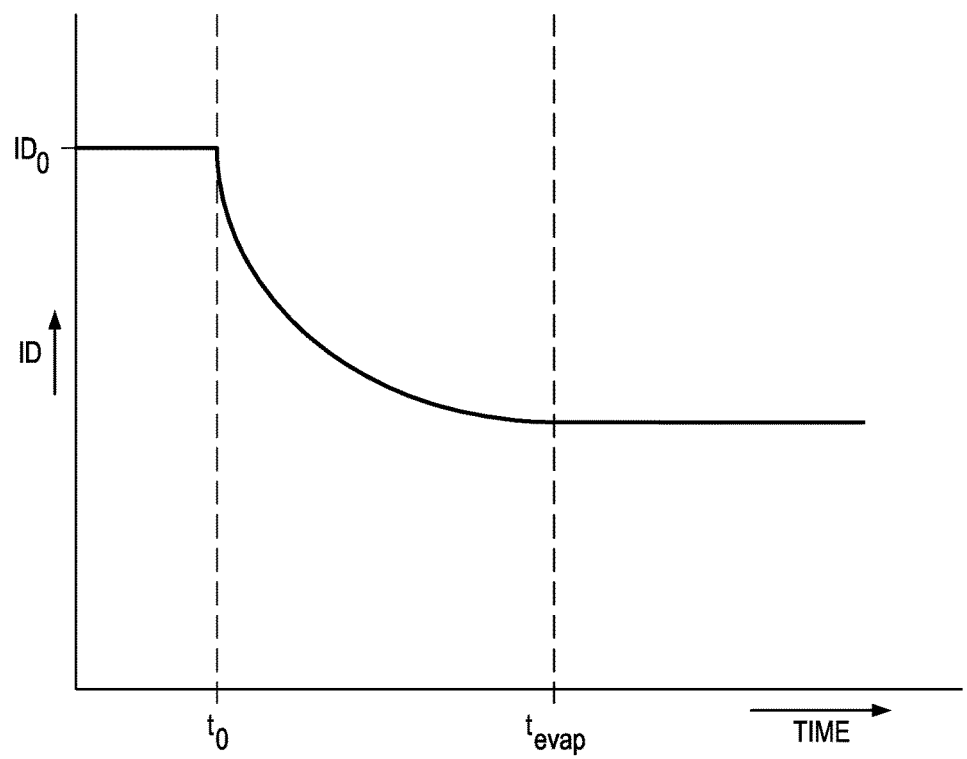

FIG. 3a illustrates an equivalent circuit for the effects of moisture and evaporation at the surface of analog floating-gate integrated circuit 20 of FIGS. 1b and 2a through 2d. As shown in FIG. 3a, this equivalent circuit includes storage capacitor 26 receiving gate voltage VG, and transistor 24 having its drain biased at voltage VD and its source at ground. The conduction path between conductive element 21 and reference conductive elements 25 provided by the dispensed moisture and the surrounding moist air from evaporation may be modeled in this equivalent circuit by the series connection of switch 50 and time-varying variable resistor 52, where the resistance of variable resistor 52 is increased by control function 54 over time. FIG. 3b qualitatively illustrates the operation of this equivalent circuit in the measurement of evaporation rate. The initial condition of the circuit of FIG. 3a, prior to time $t_0$ in FIG. 3b, has drain voltage VD and gate voltage VG both above the threshold voltage of transistor 24, while a reference voltage, for example ground, biases each of reference conductor elements 25. A high fraction (typically on the order of 90%) of the gate voltage VG will capacitively couple to floating-gate electrode 22, turning on transistor 24 and resulting in drain current $ID_0$ being conducted prior to time $t_0$. At this point in the operation, because the surface of integrated circuit 20 is dry, no conduction path is present between conductor element 21 and reference conductor elements 25. As such, floating-gate electrode 22 does not discharge to ground, and drain current ID remains constant at the level $ID_0$.

At time $t_0$, moisture is dispensed at the surface of integrated circuit 20 by moisture dispenser 30, in the form of one or more moisture droplets M. This moisture presents a conduction path between conductor element 21 and one or more of reference conductor elements 25. Referring to the equivalent circuit of FIG. 3a, switch 50 closes at time $t_0$, such that floating-gate electrode 22 is coupled to ground via resistor 52. Charge present at floating-gate electrode 22 will then conduct from conductive element 21, through the conduction path of moisture droplet M and the surrounding moist air due to evaporation of droplet M, to the ground potential at reference conductor elements 25. As charge is removed from floating-gate electrode 22, the gate potential of transistor 24 drops, causing drain current ID to drop following time $t_0$, as evident in FIG. 3*b*.

Beginning at time $t_0$, the dispensed moisture will evaporate at a rate depending on the current environment in the vicinity of the surface of integrated circuit 20. As this moisture evaporates, the conduction path between conductor element 21 and reference conductor elements 25 will become more resistive, which is modeled in the equivalent circuit of FIG. 3*a* by control function 54 causing the resistance of variable resistor 52 to increase following time $t_0$. Upon sufficient evaporation, the resistance of variable resistor 52 will effectively become infinite and no conduction path due to moisture will remain between conductor element 21 and reference conductor elements 25, at which time the loss of charge from floating-gate electrode 22 ceases. Switch 50 can be considered to be open at this point in time, shown in FIG. 3*b* as time $t_{evap}$. Once floating-gate electrode 22 is no longer being discharged, drain current ID stabilizes at its then-current value, and will remain constant as long as transistor 24 is under the same bias conditions.

According to these embodiments, the evaporation rate can be calculated from the time elapsed between the dispensing of moisture, at time $t_0$, and the stabilizing of drain current ID to a steady-state condition, at time $t_{evap}$. The steady-state level of drain current ID that is reached at time $t_{evap}$ is not particularly relevant to the determination of evaporation rate, but is more related to the amount of moisture (size of droplet M) dispensed at the surface of integrated circuit 20 (i.e., more water will reduce the initial resistance of variable resistor 52, and will also extend the time required to reach time $t_{evap}$). Calibration of the behavior of atmometer sensor 5 to an independent measurement of evaporation rate, for example by a conventional atmometer (which itself is calibrated), will enable determination of an evaporation rate, assuming the repeatable dispensing of moisture from measurement to measurement.

Referring to the equivalent circuit of FIG. 3*a*, the conduction of charge from floating-gate electrode 22 will follow an RC time constant, in which the initial value of the resistive component will depend on the size of moisture droplet M relative to the separation SEP between conductive element 21 and reference conductive element(s) 25. For the example of a floating-gate capacitance of on the order of 100 pF, a conduction path having a resistance of on the order of 10 GΩ would provide a time constant of about 1 second. Because the resistance of dry air (i.e., before moisture is dispensed) is much greater than 10 GΩ, no appreciable conduction of charge from floating-gate electrode 22 will occur, as evident in FIG. 3*b* prior to time $t_0$. On the other hand, the resistivity of liquid water with impurities is in the MΩ range, which would rapidly decay the charge from floating-gate electrode 22, well within one second in this example. It is contemplated that precise measurements of evaporation rate will be more easily attained if the time constant of the charge decay is on the order of seconds. This slower decay can be attained by a sufficiently large distance SEP between conductive element 21 and reference conductor element(s) 25 that a single moisture droplet M (e.g., of a radius on the order of 100μ) covering conductive element 21 will not extend to reference conductive element 25. This results in at least part of the conduction path being constituted by the moist air from evaporation of the droplet, which will be more resistive than the liquid droplet itself. Accordingly, it is contemplated that many implementations will select a distance SEP between reference conductive elements 25 and conductive element 21 that is sufficiently large so that the dispensed moisture droplet M will contact only conductive element 21 and not contact reference conductive elements 25. Alternatively, if a more rapid decay time is desired, a shorter distance SEP may be implemented so that the dispensed droplet M contacts both conductive element 21 and reference conductive elements 25.

Figure 4:
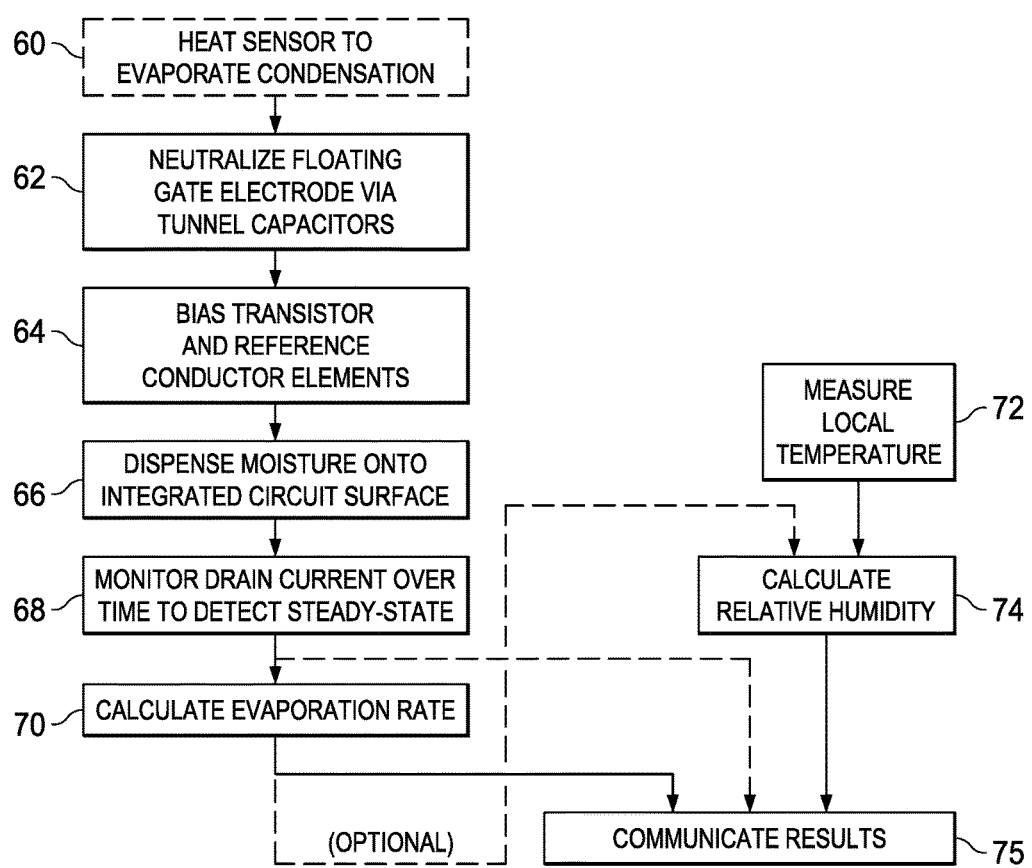
FIG. 4 is a flow diagram illustrating the operation of the atmometer sensor node of FIGS. 1a and 1b in measuring evaporation rate and, optionally, relative humidity according to embodiments.

Referring now to FIG. 4, the overall operation of atmometer system 5 of FIG. 1b in calculating an instance of an evaporation rate will now be described. As discussed above in the context of FIGS. 1a and 1b, it is contemplated that the control of the operations of atmometer system 5 and the execution of various calculations based on the results of that operation may be performed on a scheduled or automated basis, for example in a networked system of sensors and controllers deployed in the area or environment to be monitored. As such, it is contemplated that many implementations may configure control circuitry 35 within atmometer sensor 5 itself, or MCU 2 in node N for the particular sensor 5, or some combination of the two, to have the necessary and appropriate computational capacity to carry out these operations and calculations, and that such implementation will be readily apparent to those skilled in the art having reference to this specification. In any case, while the following description will be referring to the various components of atmometer system 5 and node N, those skilled in the art will recognize that such description is presented by way of example only, and that these embodiments may be realized over a wide array of architectures and systems, without undue experimentation.

Prior to beginning a measurement of evaporation rate, optional heating process 60 may be performed if desired. In process 60, heater 31 (FIG. 1b) is actuated by control circuitry 35 to heat the surface of integrated circuit 20 so as to evaporate any residual moisture at that surface from a previous measurement, and to evaporate any condensation on that surface that may have formed. As described above, heating process 60 should not affect the environmental conditions at the surface of integrated circuit 20 during the evaporation rate measurement.

In process 62, floating-gate electrode 22 is neutralized by tunnel capacitors 28p, 28n so as to have no residual charge. Process 62 may be performed by applying a pulse of either or both an appropriate negative voltage (e.g., on the order of –10 volts) to terminal TN and an appropriate positive voltage (e.g., on the order of +10 volts) at terminal TP, both relative to a ground reference voltage applied to all other nodes (gate G, source S, drain D). This operation is intended to remove any residual positive charge and residual electrons from floating-gate electrode 22. Once neutralized in process 62, floating-gate electrode 22 is at a known neutral state and may be then charged by the application of a bias voltage at gate G.

In process 64 in this embodiment, control circuitry 35 applies bias voltages to gate G, to drain D of transistor 24, and to reference conductor elements 25. For the example of an n-channel transistor 24, a positive polarity drain voltage VD above the threshold voltage of transistor 24 will be applied to drain D, and a positive polarity gate voltage VG that capacitively couples to charge floating-gate electrode 22 above the threshold voltage of transistor 24 will be applied to gate G. A reference voltage such as ground, for the case of a positive polarity gate voltage applied to floating-gate electrode 22 and thus conductor element 21, is also applied to reference conductor elements 25 in process 64. As a result of process 64, transistor 24 will conduct a constant drain current $ID_0$, with the level of that current depending on the particular bias conditions and transistor parameters.

In process 66, control circuitry 35 issues a control signal to moisture dispenser 30 to cause it to dispense moisture at the surface of integrated circuit 20, specifically to dispense moisture contacting conductor element 21. As discussed above, it is contemplated that dispensation process 66 may deposit either a single droplet or multiple droplets over the surface of integrated circuit 20. In any case, as mentioned above, it is beneficial for the size of moisture droplets M dispensed in process 66 to be controllable so as to be consistent over time, allowing calibration of atmometer sensor 5 to repeatably provide an evaporation rate measurement.

In process 68, control circuitry 35 monitors the drain current ID as conducted by transistor 24 to determine the time elapsed after the dispensing of moisture at the surface in process 66 until drain current ID reaches a stable level. As discussed above, this time elapsed to reach steady-state equilibrium indicates the rate at which moisture evaporates at the surface of integrated circuit 20 under current environmental conditions. This elapsed time is then applied to computational circuitry, such as within control circuitry 35 of atmometer sensor 5 or by ALU 10 in MCU 2 of node N, to calculate an evaporation rate in process 70. As discussed above, it is contemplated that this calculation will apply previously determined calibration data that correlates elapsed time values as monitored in process 68 to an evaporation rate, given such parameters of the moisture dispensed in process 66 as droplet size, droplet quantity, and conductivity of the dispensed water.

Upon completion of calculation process 70, the evaporation rate detected by atmometer sensor 5 may then be communicated to the appropriate destination host computer, or local or remote data base, for example by wireless or other communications carried out by transceiver 4 of node N, in process 75. These results may be communicated in process 75 immediately on a real time basis, or alternatively may be stored locally at atmometer sensor 5 or at node N for later communication or retrieval. Further in the alternative, as shown in FIG. 4, the elapsed time results of process 68 may be communicated in process 75, in which case the evaporation rate calculation of process 70 will be performed by a remote computer.

According to another embodiment in which atmometer sensor 5 is operating as a relative humidity sensor, the calculated evaporation rate is used to calculate a relative humidity of the environment at integrated circuit 20. As described in the above-incorporated Gu et al. article and its supporting information, the evaporation of a droplet of water can be considered as the diffusion of water from the surface of that droplet (i.e., where saturated) into the surrounding atmosphere in which the water vapor concentration is smaller. This gives rise to a diffusion equation:

$$\frac{\partial c}{\partial t} = D\Delta c$$

where D is the diffusivity of water vapor in the air and c is the water vapor concentration. As known in the art and as described in the Gu et al. article, the diffusivity D is dependent on the ambient temperature, and may be expressed for typical conditions as $$D(T) = 0.171T + 0.28$$

This diffusion equation allows for the derivation of a characteristic time $\tau_f$ for the "disappearance" of a water droplet, due to evaporation, as dependent on the radius of the water droplet, the diffusivity D(T) as a function of temperature, the relative humidity H (as a fraction), and the saturated water vapor concentration $c_V$ at the surface of the water droplet:

$$\tau_f \sim \frac{\rho R^2}{D(T)(1-H)c_V}$$

where ρ is the density of water. Because the characteristic time $\tau_f$ amounts to an alternative expression for the rate at which the water droplet evaporates, relative humidity H can be calculated from the evaporation rate calculated in process 70 based on the measurements obtained by atmometer sensor 5.

According to this alternative embodiment, therefore, process 72 is performed to measure or obtain measurement data of the ambient temperature in the vicinity of atmometer sensor 5. As mentioned above, an additional sensor 5 may be provided within node N to locally obtain this temperature measurement, or alternatively the temperature measurement may be communicated to node N or to such other computational circuitry in the network performing these calculations, in process 72. Upon obtaining the evaporation rate calculated in process 70 and the temperature measurement in process 72, this computational circuitry such as ALU 10 in node N or elsewhere in the network then calculates the relative humidity in process 74, for example by using the equations discussed above. The results of relative humidity calculation process 74 are then forwarded on to the appropriate destination as described above, in process 75.

As will be apparent from this description to those skilled in the art, these embodiments can provide important advantages in the measurement and evaluation of evaporation rate, more particularly in enabling the rapid and frequent measuring of evaporation rate in a repeatable and reliable manner. The ability to implement the sensing mechanism in an integrated circuit realization within an atmometer system is contemplated to facilitate the efficient and inexpensive deployment of a large number of these sensors in an environment, such as an agricultural field, and in a machine-to-machine (M2M) networked system so that the measurements can be collected in an automated manner with the results communicated and collected over a wide-area network. In addition, other calculations based on the measured evaporation rate, such as relative humidity, can be readily carried out, also in an automated and networked manner if desired.

While one or more embodiments have been described in this specification, it is of course contemplated that modifications of, and alternatives to, these embodiments, such modifications and alternatives capable of obtaining one or more of the advantages and benefits of this invention, will be apparent to those of ordinary skill in the art having reference to this specification and its drawings. It is contemplated that such modifications and alternatives are within the scope of this invention as subsequently claimed herein.

What is claimed is:

1. A method of measuring evaporation rate, comprising:
   applying a drain-to-source voltage to a floating-gate transistor in an integrated circuit;
   capacitively coupling a voltage to a floating-gate electrode in the floating-gate transistor, to establish a gate-to-source voltage at that transistor;
   then dispensing moisture at a surface of the integrated circuit at which an electrode in electrical contact with the floating-gate electrode and at least one reference electrode are exposed;
   then monitoring current conducted by the floating-gate transistor to measure an elapsed time at which the current stabilizes; and
   determining an evaporation rate responsive to the measured elapsed time.

2. The method of claim 1, further comprising neutralizing the floating-gate electrode before capacitively coupling the voltage.

3. The method of claim 2, further comprising heating the surface of the integrated circuit before applying the drain-to-source voltage and before capacitively coupling the voltage to the floating-gate electrode.

4. The method of claim 2, further comprising:
   measuring an ambient temperature in the vicinity of the integrated circuit; and
   determining a relative humidity value responsive to the evaporation rate and the measured ambient temperature.

5. The method of claim 2, wherein neutralizing the floating-gate electrode comprises biasing a first doped region serving as a first plate of a first tunnel capacitor, wherein a first portion of the floating-gate electrode serves as a second plate of the first tunnel capacitor.

6. The method of claim 5, wherein neutralizing the floating-gate electrode further comprises biasing a second doped region serving as a first plate of a second tunnel capacitor, wherein a second portion of the floating-gate electrode serves as a second plate of the second tunnel capacitor;
   wherein the first and second doped regions are of opposite conductivity type from one another; and
   wherein the first and second doped regions are biased with voltages of opposite polarity from one another as a result of the biasing.

7. An integrated circuit comprising:
   source and drain doped regions formed at a semiconductor surface of a body, and separated from one another by a channel region at the surface;
   a gate dielectric film disposed over the surface;
   a floating-gate electrode overlying the gate insulator film, the floating-gate electrode having a first portion overlying the channel region to serve as a gate electrode for a transistor comprised of the source and drain doped regions, and having a second portion;
   a conductive plate disposed over the second portion of the floating-gate electrode and separated therefrom by a capacitor dielectric film, to form a storage capacitor;
   a first conductor element in electrical contact with the floating-gate electrode, and exposed to the atmosphere at the surface of the integrated circuit; and
   one or more reference conductor elements exposed to the atmosphere at the surface of the integrated circuit near the first conductor element, and adapted to be coupled to a reference voltage.

8. The integrated circuit of claim 7, further comprising:
   a first doped region of a first conductivity type disposed at the surface at a location underlying a third portion of the floating-gate electrode, and separated therefrom by a tunnel dielectric film, to form a first tunnel capacitor.

9. The integrated circuit of claim 8, further comprising:
   a second doped region of a second conductivity type disposed at the surface at a location underlying a fourth portion of the floating-gate electrode, and separated therefrom by the tunnel dielectric film, to form a second tunnel capacitor.

10. An atmometer system, comprising:
   an integrated circuit, comprising:
   a floating-gate electrode;
   a metal-oxide-semiconductor (MOS) transistor having source and drain regions disposed in a semiconductor surface of the integrated circuit and separated from one another by a channel region, wherein a first portion of the floating-gate electrode is disposed over the channel region to serve as a gate electrode of the MOS transistor;

a storage capacitor having a first plate comprised of a second portion of the floating-gate electrode, and a second plate separated from the first plate by a dielectric film;

a first conductor element in electrical contact with the floating-gate electrode, and exposed at a surface of the integrated circuit; and one or more reference conductor elements disposed at the surface of the integrated circuit near the first conductor element, and coupled to a reference voltage node; and control circuitry, coupled to the drain region of the MOS transistor and to the second plate of the storage capacitor, the control circuitry being configured to bias the gate of the MOS transistor, output a moisture dispensing control signal, and measure current conducted by the MOS transistor.

11. The atmometer system of claim 10, further comprising a heater disposed near or in the integrated circuit and coupled to the control circuitry.

12. The atmometer system of claim 11, wherein the heater comprises a polysilicon resistor.

13. The atmometer system of claim 10, wherein the integrated circuit further comprises a first tunnel capacitor having a first plate comprised of a third portion of the floating-gate electrode, and a second plate separated from the first plate by a dielectric film and coupled to the control circuitry.

14. The atmometer system of claim 13, wherein the integrated circuit further comprises:

a second tunnel capacitor, having a first plate comprised of a fourth portion of the floating-gate electrode, and a second plate separated from the first plate by a dielectric film and coupled to the control circuitry;

wherein the second plate of the first tunnel capacitor comprises a doped semiconductor region of a first conductivity type;

and wherein the second plate of the second tunnel capacitor comprises a doped semiconductor region of a second conductivity type.

15. The atmometer system of claim 14, wherein the control circuitry comprises:

processor circuitry configured to execute a sequence of operations comprising:

biasing the second plates of each of the first and second tunnel capacitors to neutralize a potential of the electrode;

then biasing the transistor by applying a voltage to the second plate of the storage capacitor and a drain-to-source voltage across the transistor;

then controlling a moisture dispenser to dispense moisture at the surface of the integrated circuit at least partially in response to the moisture dispensing control signal; and measuring current conducted by the transistor over an interval of time following the controlling operation to detect an elapsed time at which the current stabilizes.

16. The atmometer system of claim 15, further comprising a communications transceiver coupled to the control circuitry and configured to communicate signals responsive to the elapsed time.

17. The atmometer system of claim 16, wherein the sequence of operations further comprises:

determining an evaporation rate responsive to the measured current;

receiving a temperature measurement; and determining a relative humidity responsive to the evaporation rate and the temperature measurement.

* * * * *